United States Patent [19]

Koyama et al.

[11] Patent Number: 5,087,421

[45] Date of Patent: Feb. 11, 1992

[54] MULTILAYERED ASSAY ELEMENT

[75] Inventors: Mikio Koyama; Satoshi Kawakatsu; Tomoji Akashi; Kenichiro Okaniwa, all of Tokyo, Japan

[73] Assignee: Konica Corporation, Tokyo, Japan

[21] Appl. No.: 353,942

[22] Filed: May 19, 1989

[30] Foreign Application Priority Data

May 20, 1988 [JP] Japan .................................. 63-124479

[51] Int. Cl.$^5$ ............................................. G01N 21/29
[52] U.S. Cl. ........................................ 422/56; 422/57; 422/58; 436/166
[58] Field of Search ..................................... 422/56-58; 430/216, 213; 8/555, 551; 436/166

[56] References Cited

U.S. PATENT DOCUMENTS

| 3,271,147 | 9/1966 | Bush ....................................... 430/216 |
| 3,992,158 | 11/1976 | Przybylowicz et al. .............. 422/57 |
| 4,042,335 | 8/1977 | Clement ................................ 422/56 |
| 4,069,017 | 1/1978 | Wu et al. ............................... 422/56 |

Primary Examiner—Robert J. Warden
Assistant Examiner—Lyle A. Alexander
Attorney, Agent, or Firm—Finnegan, Henderson, Farabow, Garrett, and Dunner

[57] ABSTRACT

Disclosed is a multilayered assay element in which the influence by the bilirubin contained in the sample fluid is substantially eliminated. The assay element of the present invention contains a bilirubin-trapping agent of the formula $$-(A)_x-(B)_y-(C)_z- \qquad [I]$$

(wherein A represents a monomer unit having a copolymerizable unsaturated double bond and a quaternary ammonium salt, B represents a monomer unit having a copolymerizable unsaturated double bond, C represents a monomer unit having at least two copolymerizable unsaturated double bonds and x, y and z represents the number mol % of 100–10, 90–0 and 10–0, respectively) which bilirubin-trapping agent is incorporated in a region which is upper than the reagent layer.

4 Claims, No Drawings

MULTILAYERED ASSAY ELEMENT

BACKGROUND OF THE INVENTION

I. Field of the Invention

This invention relates to an assay element for determining the amount of a target substance contained in a sample fluid such as blood.

II. Description of the Related Art

Various immunoassay systems for quantifying a target substance such as various drugs, metabolites, hormones and vitamines, which is contained in a sample fluid such as blood have been developed. The principle of most of these systems is based on the immunoassay, especially enzyme immunoassay and multilayered assay films with high precision which offer simplified operations have been developed. These multilayered assay films comprise a transparent support, a reagent layer formed on the support and a porous spreading layer formed on the reagent layer. Various reagents which are necessary for the immunoassay are contained in the reagent layer. In operation, the sample fluid which may contain the target substance which is to be quantified is dropped on the spreading layer and the dropped fluid is uniformly spread in the spreading layer so that equal amount of the sample fluid per a unit area is supplied to the reagent layer. In the reagent layer, prescribed immunological reaction and the enzyme reaction are carried out. In the enzyme immunoassay, in most cases, coloring reaction is carried out by the aid of an enzyme, and the target substance is quantified by measuring the degree of the generation of color. With the multilayered assay film, this is conducted by impinging a light with a prescribed wavelength on the backside of the transparent support and then measuring the reflection density of the light. In a typical example of the conventional multilayered assay element, in the reagent layer, are contained a substance (antibody or antigen) which specifically reacts with the target substance to be quantified (antigen or antibody), the target substance labelled with a coenzyme such as FAD, glucose oxidase which is an apo enzyme which is activated by the coenzyme and glucose which is the substrate of the glucose oxidase, as well as peroxidase which generates color from hydrogen peroxide generated from glucose by the action of the glucose oxidase and 4-aminoantipyrine which is required for the coloring reaction, and the quantification of the target substance contained in the sample fluid is carried out by impinging a light with a specific wavelength on the backside of the transparent support and by measuring the reflection density of the light.

On the other hand, a bile pigment called bilirubin which has orange-yellow color is contained in the blood. Bilirubin is a normal metabolite which is produced mainly by the degradation of heme. The yellowness of the human serum is due to the existence of bilirubin and the bilirubin level is especially high in the blood of the patients suffering from porphyria. Since bilirubin is an orange-yellow pigment, if bilirubin is contained in the reagent layer of the above-mentioned multilayered assay element, the measurement of the generated color in the enzyme immunoassay is hindered. That is, when the wavelength of the color generated by the enzyme reaction is near the wavelength of the color of bilirubin, it is difficult to distinguish the color generated by the enzyme reaction from the color due to the existence of bilirubin, so that the precision of the immunoassay is degraded. Further, it is reported that bilirubin reacts with hydrogen peroxide, so that the precision of the enzyme immunoassay in which the generation of hydrogen peroxide is utilized is degraded. In particular, although blood can be analyzed without dilution with the recently developed dry chemistry type multilayered immunoassay elements, in this case, since the bilirubin level is high in the non-diluted blood, the degradation of the precision of the assay due to the existence of bilirubin is a serious problem. Especially, it is difficult to analyze the blood from the patients suffering from porphyria, in which bilirubin is contained at a high level, without diluting the blood. Thus, in such a case, the troublesome dilution operation is required.

SUMMARY OF THE INVENTION

Accordingly, the object of the present invention is to provide a multilayered assay element with which the precision of the assay is not substantially degraded by the existence of bilirubin in the sample fluid.

The present inventors intensively studied to find that the diffusion of bilirubin into the reagent layer can be inhibited by incorporating a bilirubin-trapping agent in a region which is upper than the reagent layer, thereby the degradation of the precision of the assay due to bilirubin can be prevented, to complete the present invention.

That is, the present invention provides a multilayered assay element comprising a support; a reagent layer formed on the support; a spreading layer formed on the reagent layer and bilirubin-trapping agent of the formula [I],

 [I]

(wherein A represents a monomer unit having a copolymerizable unsaturated double bond and a quaternary ammonium salt, B represents a monomer unit having a copolymerizable unsaturated double bond, C represents a monomer unit having at least two copolymerizable unsaturated double bonds and x, y and z represents the number mol% of 100-10, 90-0 and 10-0, respectively) which bilirubin-trapping agent is incorporated at a region which is upper than the reagent layer.

With the assay element of the present invention, since the bilirubin is trapped by the bilirubin-trapping agent located in a region which is upper than the reagent layer, bilirubin does not substantially diffuse into the reagent layer. Therefore, the precision of the assay is not degraded by the existence of bilirubin. Thus, even a sample fluid containing high level of bilirubin, such as the blood from the patient suffering from porphyria, can be assayed without diluting the sample. Thus, the troublesome diluting operations can be omitted, so that the present invention strongly helps the rapid clinical examination.

DETAILED DESCRIPTION OF THE PREFERRED EMBODIMENTS

The bilirubin-trapping agent used in the present invention is represented by the above-described formula [I]. In the formula [I], A represents a monomer unit which has a copolymerizable double bond and a quaternary ammonium salt. Bilirubin is considered to be bound to the quaternary ammonium salt. Therefore, A is an indispensable unit in the compound of the formula [I], and the content thereof in the compound (represented by "x" in the formula [I]) is 10-100 mol%. Preferred examples of the unit A may include those represented by the following formulae [II] to [VII]:

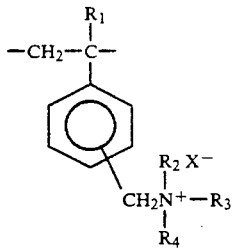

(wherein $R_1$ represents hydrogen atom or methyl group, $R_2$, $R_3$ and $R_4$, the same or different, represent alkyl, aralkyl, cycloalkyl or cycloaralkyl group, $X^-$ represents a monovalent anion),

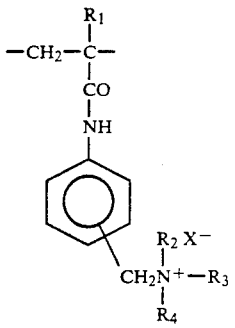

(wherein $R_1$, $R_2$, $R_3$, $R_4$ and $R^-$ represent the same meaning as in the formula [II]),

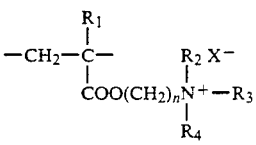

(wherein $R_1$, $R_2$, $R_3$, $R_4$ and $R^-$ represent the same meaning as in the formula [II], n represents an integer of 1 to 4),

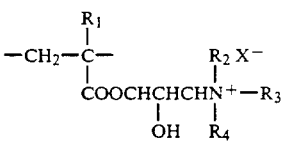

wherein $R_1$, $R_2$, $R_3$, $R_4$ and $X^-$ represent the same meaning as in the formula [II]),

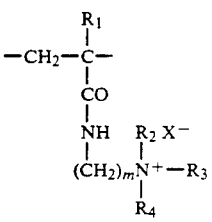

(wherein $R_1$, $R_2$, $R_3$, $R_4$ and $X^-$ represent the same meaning as in the formula [II], m represents an integer of 1 to 4),

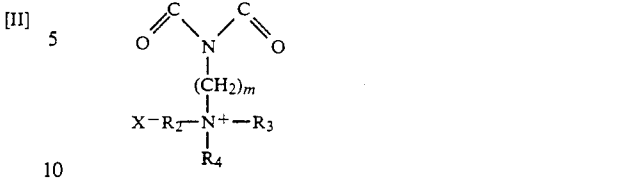

(wherein $R_1$, $R_2$, $R_3$, $R_4$ and $X^-$ represent the same meaning as in the formula [II], m represents the same meaning as in the formula [VI]).

In the formula [I], B represents a monomer unit which has a copolymerizable double bond. The unit B serves to optionally control the physical properties of the compound of the formula [I]. For example, by appropriately selecting B, hydrophobicity may be given to the compound, or glass transition point may be raised so as to promote the film-forming property of the compound. Further, the unit B may also be selected so as to inhibit the undesired migration of the compound in the assay element. Thus, the unit B is not indispensable in the compound of the formula [I], and the content thereof in the compound (represented by "y" in the formula [I]) is 0-90 mol%, preferably 0-70 mol%. Preferred examples of the unit B may include styrene and derivatives thereof such as methyl styrene, hydroxystyrene and chloro styrene; acrylates and methacrylates such as methyl acrylate, ethyl acrylate, n-butyl acrylate, methyl methacrylate, ethyl methacrylate and n-butyl methacrylate; acrylonitriles and methacrylonitriles; halogenated olefins such as vinyl chloride and vinylidene chloride; dienes such as butadiene, isoprene and dimethyl butadiene; amides such as acrylamide, methacrylamide, N-methylacrylamide, N,N-dimethylacrylamide and diacetone acrylamide; saturated aliphatic vinyl esters such as vinyl acetate and vinyl butyrate; and N-vinyl pyrrolidone.

In the formula [I], C represents a monomer unit which has at least two copolymerizable double bonds. The unit C serves to make the compound of the formula [I] in the form of latex, or to control the molecular weight of the compound to a desired range. The unit C is not indispensable in the compound of the formula [I] and the content thereof in the compound (represented by "z" in the formula [I]) is 0-10 mol%, preferably 0-6 mol%. Preferred example of the unit C includes divinyl benzene.

The compound of the formula [I] adsorbs bilirubin on the unit A, so that the molecular weight thereof is not restricted. However, since it is necessary that the bilirubin-trapping agent remain in the region which is upper than the reagent layer and so the diffusion thereof from the prescribed region should be prevented, the bilirubin-trapping agent preferably has a number molecular weight of not less than 5000, or preferably is in the form of latex.

As mentioned above, since only the unit A is indispensable to the bilirubin-trapping agent, the order of sequence of the units A, B and C is not important and may be of any order. Thus, the compound of the formula [I] may be a random copolymer or block copolymer, and may be straight or grafted.

The compound of the formula [I] per se as well as the manufacturing process thereof is known and is used in the films for so called "instant cameras". The compound of the formula [I] is described in detail in U.S. Pat. Nos. 3,271,147, 3,770,439, 3,958,995, British Patent 1,366,869, British Patent 1,366,870 and Japanese Patent Disclosure (Kokai) No. 22766/80.

In the multilayered assay element of the present invention, it is required that the bilirubin-trapping agent exist at a location which is upper than the reagent layer. This can be attained by incorporating the bilirubin-trapping agent in the spreading layer. The spreading layer which serves to uniformly spread the sample fluid so as to supply uniform amount of sample to the reagent layer thereunder is conventionally made of a fibrous material. Thus, by forming the spreading layer with a fibrous material bound together with a binder and by incorporating the bilirubin-trapping agent in the binder, the above-described incorporation of bilirubin in the spreading layer can be attained. In this case, the content of the bilirubin-trapping agent in the binder may preferably be not less than 10% by weight, more preferably 25-85% by weight. Preferred examples of the fibrous material for constituting the spreading layer may include, as in the conventional assay elements, pulp, cellulose powder and natural, synthetic and semisynthesized fibers of various plants, animals, minerals and artificial products such as cotton, hemp, silk, wool, chitin, chitosan, cellulose ester, viscose rayon, copper-ammonia rayon, polyamides (e.g., 6-nylon, 6,6-nylon and the like), polyesters (e.g., polyethylene terephthalate and the like), polyolefins (polypropyrene, vinylon and the like), glass and asbestos. These materials may be employed individually or in combination. As the binder, hydrophobic polymers or copolymers such as styrene-glycidylmethacrylate copolymer, or hydrophilic polymers or copolymers such as poly-N-vinylpyrrolidone may appropriately be employed, as in the conventional multilayered assay elements. The ratio of the fibrous material to the binder (containing the bilirubin-trapping agent) is usually 98:2 to 80:20 based on weight, preferably 95:5 to 85:15.

Alternatively, a separate layer containing the bilirubin-trapping agent optionally together with the binder may be provided at a location which is upper than the reagent layer. Thus, the spreading layer may not necessarily be formed directly on the reagent layer but may indirectly be formed on the reagent layer via this separate layer containing the bilirubin-trapping agent.

In the multilayered assay element of the present invention, what is required is only that the bilirubin-trapping agent be contained in a region upper than the reagent layer so that the bilirubin contained in the sample fluid is trapped by the bilirubin-trapping agent before reaching the reagent layer. Therefore, the constitution of the reagent layer and the support which are located lower than the bilirubin-trapping agent is not critical in the present invention and is not limited at all. In other words, the present invention can be applied to any of the multilayered assay elements with which the entering of bilirubin to the reagent layer is undesired, so that the target substance to be determined, the principle of assay and the reagents contained in the reagent layer are not limited at all. The multilayered assay element of the present invention may advantageously be applied, for example, for the quantification of creatinine, creatin (by the method in which sarcosine is utilized), -amylase (p-nitrophenyl oligosasscharide method) and alkaline phosphatase (p-nitrophenyl phosphate method) as well as for ARIS TDM (Apo-enzyme reactitative immunoassay system). In the immunoassay element of the present invention, immunogical reaction layer in which an immunological reaction is carried out may separately be formed between the reagent layer and the spreading layer, as in the conventional multilayered immunoassay elements.

The reagents contained in the reagent layer of the element of the present invention are reagents for analysis which concern the detection reaction. That is, the reagent layer may contain an antibody, apo-glucose oxidase and a composition for detecting hydrogen peroxide.

For example, in one embodiment of the present invention, on a transparent support, are laminated a first reagent layer containing POD, a colorant and a labelled compound, a second reagent layer called an immunological reaction layer containing an antibody and apo-glucose oxidase, and the spreading layer, and the bilirubin-trapping agent defined in the present invention is contained in a layer which is located upper than the second reagent layer. Thus, the bilirubin-trapping agent is contained in, for example, the spreading layer or a separate layer containing the bilirubin-trapping agent may be formed between the spreading layer and the second reagent layer.

The present invention can be attained by employing the above-described structure. It should be noted, however, the above-described three-layered structure is one embodiment of the present invention and the scope of the present invention is not restricted thereto.

The multilayered assay element of the present invention may be used in the same manner as the conventional multilayered assay element. That is, a sample fluid such as blood and bile, which may contain bilirubin is dropped on the spreading layer and the color generated in the reagent layer is measured.

The present invention will now be described in more detail by way of examples thereof. It should be noted that the examples are presented for the illustration purpose only and should not be interpreted in any restrictive way. Unless otherwise specified, all % are by weight.

EXAMPLE 1

On a support made of a transparent polyethylene terephthalate film, a solution having the following composition was applied using a doctor blade having a gap of 250 μm:

Reagent Layer-1

| Deionized Gelatin | 15 g |
| --- | --- |
| Triton X-100 (surfactant commercially available from Room and Haas) | 1.5 g |
| Glucose | 2.0 g |
| Gantrez ES-225 (copolymer of methyl vinyl ether and monoethyl maleate commercially available from GAF Co., Ltd.) | 10 g |
| 3,3',5,5'-tetramethylbenzidine | 300 mg |
| FAD-labelled Theophyllin | 15 μg |
| 1.5M Phosphate-citrate Buffer (pH 5.0) | 20 ml |
| 1,2-bis(vinylsulfonyl)ethane | 100 mg |
| Distilled Water | 100 ml |
| Peroxidase | 10,000 U |

The thickness of the reagent layer after drying was about 20 um.

Reagent Layer-2

On the above-described reagent layer-1, a solution having the following composition was applied using a doctor blade with a gap of 500 μm;

| | Avicel (microcrystalline cellulose commercially available from Asahi Chemicals) | 11.0 g |
|---|---|---|
| | Polyvinylpyrrolidone | 1.8 g |
| | Triton X-100 | 0.4 g |
| | Anti-theophylline Antibody/Bovine Serum Alubumin Lyophilized Powder | 200 mg |
| | Apoglucose Oxidase Containing Anti-glucose Oxidase Antibody/Bovine Serum Alubumin Lyophilized Powder | 380 mg |
| | n-butanol | 34.0 g |

The thickness of the reagent layer-2 after drying was about 150 μm.

Porous Spreading Layer

On the reagent layer-2, a solution with the following composition was applied using a doctor blade with a gap of 500 μm.

| Cellulose Powder D | 18 g |
|---|---|
| Triton X-100 | 1.8 g |
| Polyvinylpyrrolidone | 1.8 g |
| Compound (I)–(V) (the content is shown in Table 1) | |
| n-butanol | 68 g |

The thickness of the spreading layer after drying was about 250 μm.

The prepared assay element was cut into pieces sizing 1.5 cm×1.5 cm and was mounted on a plastic mount sizing 2.5 cm×2.8 cm having an opening with a diameter of 7 mm.

TABLE 1

| | Assay Element of the Invention | | | | | Comparative Element 1 |
|---|---|---|---|---|---|---|
| | 1 | 2 | 3 | 4 | 5 | |
| Polyvinyl-pyrrolidone | 50% | 50% | 50% | 50% | 50% | 100% |
| Compound (I) | 50% | | | | | |
| Compound (II) | | 50% | | | | |
| Compound (III) | | | 50% | | | |
| Compound (IV) | | | | 50% | | |
| Compound (V) | | | | | 50% | |

Compound (I)

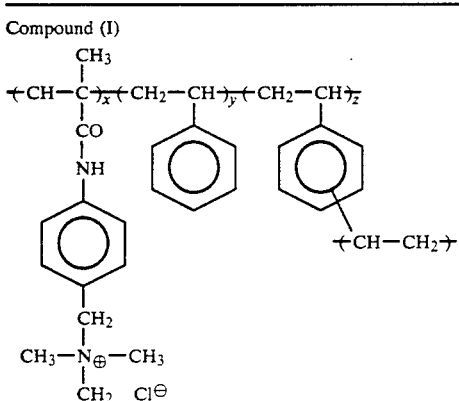

x:y:z = 49:48:4

Compound (II)

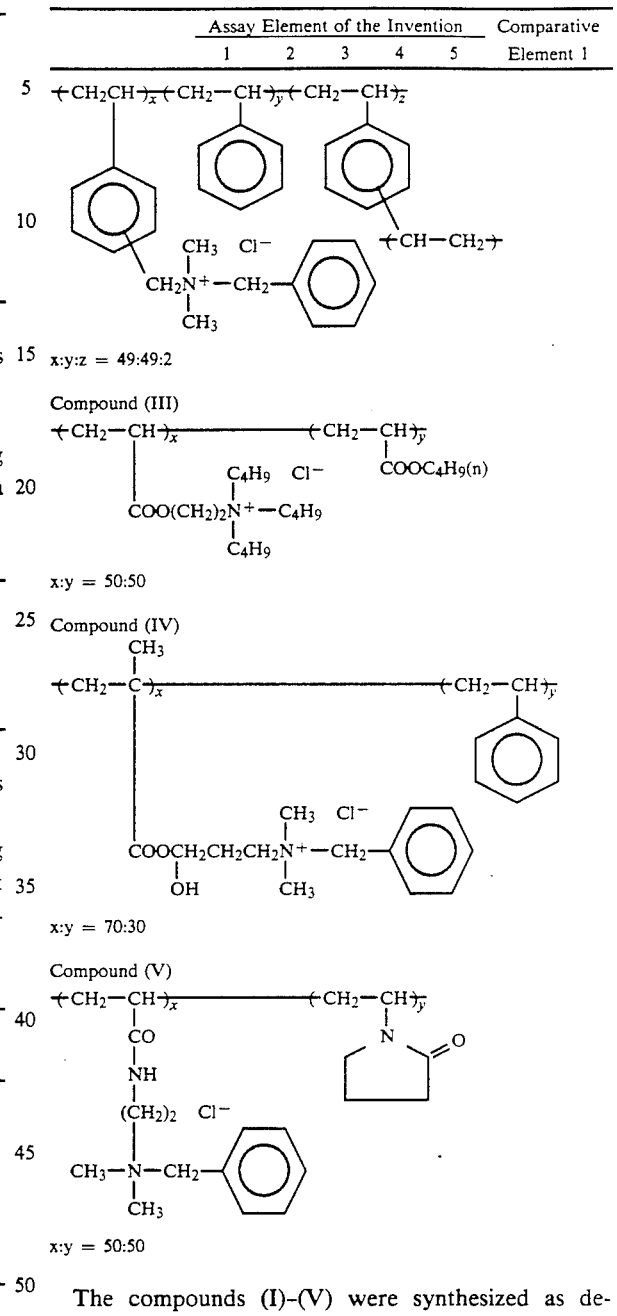

The compounds (I)–(V) were synthesized as described in U.S. Pat. No. 3,271,147 or Japanese Patent Disclosure (Kokai) No. 22766/80.

By appropriately mixing Lyphocheck TDM Control Level I, II and III (commercially available from Bio-Rad Laboratories), sera with varying theophyllin level were prepared. The theophyllin level in the thus prepared sera was determined by using TDX (commercially available from Abbott Laboratories).

Ten microliters of each of the sera was dropped on each of the assay elements 1–5 of the present invention and the comparative element 1. The elements were then kept at 37° C. in the sealed condition. Light with a wavelength of 650 nm was impinged on the backside of the support every 30 seconds and the reflection density was measured from the side of the support after 3 minutes and 7 minutes from the dropping of the sample serum. The change in the reflection density was plotted with respect to the theopyllin level in the sample to prepare a calibration curve.

To Lyphocheck TDM Control Level II (with a theophyllin level of 14.5 μg/ml), Bilirubin Standard Conc. (commercially available from Nippon Shoji Co., Ltd., Japan) was added so as to attain the bilirubin level of 0, 1.5, 3, 5, 10, 15 or 20 mg/dl (the theophyllin level was 14.0 μg/ml).

The thus prepared samples were subjected to the quantification of theophyllin using the assay elements prepared as described above. The measured reflection density was compared with the calibration curve prepared as described above to determine the theophellin level in the sample.

The results are shown in Table 2.

TABLE 2

|  | Bilirubin Level (mg/dl) | | | | | | |
| --- | --- | --- | --- | --- | --- | --- | --- |
|  | 0 | 1.5 | 3 | 5 | 10 | 15 | 20 |
| Element of the Invention | | | | | | | |
| 1 | 14.5 | 14.5 | 14.4 | 14.5 | 14.3 | 13.9 | 13.0 |
|  | | (100) | (99) | (100) | (99) | (96) | (90) |
| 2 | 14.5 | 14.4 | 14.2 | 14.1 | 13.8 | 13.2 | 12.9 |
|  | | (99) | (98) | (97) | (95) | (91) | (89) |
| 3 | 14.5 | 14.5 | 14.5 | 14.3 | 13.9 | 14.0 | 13.2 |
|  | | (100) | (100) | (99) | (96) | (97) | (91) |
| 4 | 14.5 | 14.5 | 14.2 | 14.0 | 13.7 | 13.6 | 12.7 |
|  | | (100) | (98) | (97) | (94) | (94) | (88) |
| 5 | 14.5 | 14.3 | 14.2 | 14.0 | 13.6 | 13.0 | 12.5 |
|  | | (99) | (98) | (97) | (94) | (90) | (86) |
| Comparative Element 1 | 14.5 | 14.0 | 13.2 | 12.6 | 11.4 | 10.8 | 9.1 |
|  | | (97) | (91) | (87) | (79) | (74) | (63) |

(The upper low indicates the theophyllin level (μg/ml), and the numbers in parentheses mean the % theophyllin level taking the measured theophyllin level of the sample containing no bilirubin as 100%)

As is apparent from Table 2, the assay elements of the present invention are not so influenced by the existence of bilirubin as the conventional comparative element 1.

EXAMPLE 2

The assay elements 6–8 and comparative element 2 were prepared in the same manner as in Example 1 except that the solution for forming the spreading layer had the following composition:

Porous Spreading Layer

| | |
| --- | --- |
| Cellulose Powder D (Advantech commercially available from Toyo Filter Paper Co., Ltd.) | 18 g |
| Triton X-100 | 1.8 g |
| Polyvinylpyrrolidone | |
| Compound (VI) | Contents are shown in Table 3 |
| Cetyltrimethyl Ammonium | |
| n-butanol | 68 g |

The thickness of the spreading layer after drying was about 250 um.

TABLE 3

|  | Assay Element of the Invention | | | Comparative Element |
| --- | --- | --- | --- | --- |
|  | 6 | 7 | 8 | 2 |
| Polyvinyl-pyrrolidone | 75% | 50% | | 90% |
| Compound (VI) | 25% | 50% | 100% | |
| Cetyltrimethyl Ammonium Chloride | | | | 10% |

Compound (VI)

TABLE 3-continued

|  | Assay Element of the Invention | | | Comparative Element |
| --- | --- | --- | --- | --- |
|  | 6 | 7 | 8 | 2 |

$$\begin{array}{c} \mathrm{-(CH_2-CH)_x-\ \ \ -(CH_2-CH)_y-} \\ | \\ \mathrm{CO} \\ | \\ \mathrm{NH} \end{array}$$

with phenyl ring bearing $\mathrm{CH_2N^+(CH_3)_2CH_2-}$ (quaternary ammonium with Cl$^-$), and pyrrolidone on the y unit.

x:y = 40:60

The compound (VI) was prepared according to the method described in U.S. Pat. No. 3,271,147 or Japanese Patent Disclosure (Kokai) No. 22766/80.

The thus prepared assay elements were cut into pieces sizing 1.5 cm × 1.5 cm, and a plastic mount sizing 2.5 cm × 2.8 cm having an opening with a diameter of 7 mm was mounted on the side of the support and on the side of the spreading layer of the element. Using Lyphocheck Drug Free Serum (commercially available from Bio-Rad Laboratories) and Lyphocheck TDM Control Level I, II and III, calibration curve was prepared in the same manner as in Example 1 (the theophyllin level in the samples was 0, 4.6, 14.3 or 28.6 μg/ml). Taking the reflection density obtained by assaying the sample containing no theophyllin as 100, the relative reflection densities of each sample were determined, which are shown in Table 4.

TABLE 4

|  | Theophylline Level (μg/ml) | | | |
| --- | --- | --- | --- | --- |
|  | 0 | 4.6 | 14.3 | 28.6 |
| Element of the Invention | | | | |
| 6 | 100 | 129 | 168 | 215 |
| 7 | 100 | 128 | 172 | 223 |
| 8 | 100 | 130 | 183 | 239 |
| Comparative Element 2 | 100 | 106 | 116 | 128 |

Further, the influence by bilirubin was examined as in Example 1. The results are shown in Table 5.

TABLE 5

|  | Bilirubin Level (mg/dl) | | | | | | |
| --- | --- | --- | --- | --- | --- | --- | --- |
|  | 0 | 1.5 | 3 | 5 | 10 | 15 | 20 |
| Element of the Invention | | | | | | | |
| 6 | 14.5 | 14.3 | 14.3 | 14.2 | 13.8 | 13.5 | 12.9 |
|  | | (99) | (99) | (98) | (95) | (93) | (89) |
| 7 | 14.5 | 14.4 | 14.3 | 14.1 | 14.0 | 13.7 | 13.0 |
|  | | (99) | (99) | (97) | (97) | (94) | (90) |
| 8 | 14.5 | 14.5 | 14.4 | 14.3 | 14.1 | 13.8 | 13.2 |
|  | | (100) | (99) | (99) | (97) | (95) | (91) |
| Comparative Element 2 | 14.5 | 12.1 | 10.9 | 10.8 | 11.0 | 9.6 | 8.9 |
|  | | (83) | (75) | (74) | (76) | (66) | (61) |

(The uppper low indicates the theophyllin level (μg/ml), and the numbers in parentheses mean the % theophyllin level taking the measured theophyllin level of the sample containing no bilirubin as 100%.)

As is apparent from Tables 4 and 5, the assay elements of the present invention had higher sensitivity than the comparative element 2 and the influence by bilirubin is smaller in the elements of the present invention than in the comparative element 2.

EXAMPLE 3

The solutions for forming the reagent layer-1, reagent layer-2 and the spreading layer, which had the following compositions were prepared:

|  | Solution No. | | | |
| --- | --- | --- | --- | --- |
|  | R-1 | R-2 | R-3 | R-4 |
| Deionized Gelatin | 15 g | 7.5 g | 7.5 g | 15 g |
| Peroxidase | 10,000 U | 10,000 U | 10,000 U | 10,000 U |
| 3,3',5,5'-tetramethylbenzidine | 300 mg | 300 mg | 300 mg | 300 mg |
| Gantrez ES-225 | 10 g | 10 g | 10 g | 10 g |
| Glucose | 20 g | 20 g | 20 g | 20 g |
| FAD-labelled Theophyllin | 15 μg | 15 μg | 15 μg | 15 μg |
| 1.5M Phosphate/citrate Buffer (pH 5.0) | 20 ml | 20 ml | 20 ml | 20 ml |
| Compound (I) | — | 7.5 g | — | — |
| Compound (II) | — | — | 7.5 g | — |
| Dodecyltrimethyl Ammonium Chloride | — | — | — | 3.0 g |
| Triton X-100 | 1.5 g | 1.5 g | 1.5 g | 1.5 g |
| 1,2-bis(vinylsulfonyl)ethane | 100 mg | 100 mg | 100 mg | 100 mg |
| Distilled Water | 100 ml | 100 ml | 100 ml | 100 ml |

|  | Solution No. | | | | |
| --- | --- | --- | --- | --- | --- |
|  | I-1 | I-2 | I-3 | I-4 | I-5 |
| Avicel | 11 g | 11 g | 11 g | 11 g | 11 g |
| Polyvinylpyrrolidone | 1.8 g | — | 0.9 g | 0.9 g | 1.8 g |
| Rubiscol VA-28 (vinylpyrrolidone/vinyl acetate = 2/8, commercially available from BASF) | — | 1.8 g | — | — | — |
| Compound (I) | — | — | 0.9 g | — | — |
| Compound (II) | — | — | — | 0.9 g | — |
| Dodecyltrimethyl Ammonium Chloride | — | — | — | — | 0.3 g |
| Anti-theophyllin/Bovine Serum Albumin Lyophilized Powder | 200 mg | 200 mg | 200 mg | 200 mg | 200 mg |
| Anti-glucose Oxidase-containing Apo Glucose/Bovine Serum Albumin Lyophilized Powder | 300 mg | 300 mg | 300 mg | 300 mg | 300 mg |
| Triton X-100 | 0.4 g | 0.4 g | 0.4 g | 0.4 g | 0.4 g |
| n-butanol | 34.0 g | 34.0 g | 34.0 g | 34.0 g | 34.0 g |

Porous Spreading Layer

|  | Solution No. | | | |
| --- | --- | --- | --- | --- |
|  | S-1 | S-2 | S-3 | S-4 |
| Cellulose Powder D | 18 g | 18 g | 18 g | 18 g |
| Polyvinylpyrrolidone | 3.6 g | 1.8 g | 1.8 g | 1.8 g |
| Compound (I) | — | 1.8 g | — | — |
| Compound (II) | — | — | 1.8 g | — |
| Compound (III) | — | — | — | 1.0 g |
| n-butanol | 68 g | — | — | — |

The reagent layer-1, the reagent layer-2 and the spreading layer were laminated using the solutions described above according to Table 6 on the support film as in Example 1.

TABLE 6

| Assay Element No. | Reagent Layer-1 | Reagent Layer-2 | Spreading Layer |
| --- | --- | --- | --- |
| 9 | R-1 | I-1 | S-1 |
| 10 | R-1 | I-1 | S-2 |
| 11 | R-1 | I-1 | S-3 |
| 12 | R-1 | I-1 | S-4 |
| 13 | R-1 | I-2 | S-1 |
| 14 | R-1 | I-2 | S-2 |
| 15 | R-1 | I-2 | S-3 |
| 16 | R-1 | I-2 | S-4 |
| 17 | R-1 | I-3 | S-1 |
| 18 | R-1 | I-4 | S-1 |
| 19 | R-1 | I-5 | S-1 |
| 20 | R-2 | I-1 | S-1 |
| 21 | R-3 | I-1 | S-1 |
| 22 | R-4 | I-1 | S-1 |

The wet thickness of the reagent layer-1, the reagent layer-2 and the spreading layer was about 250 μm, about 500 μm and about 500 μm, respectively, and the thickness of these layers after drying was about 20 μm, about 150 μm and about 250 μm, respectively.

These assay elements were mounted on the plastic mount as in Example 1. On each element, 10 μl of Lyphocheck TDM Control Level I and III having a theophyllin level (determining by TDX) of 5.3 μg/ml and 28 μg/ml, respectively, was dropped. After 3 minutes and 7 minutes from the dropping of the sample, the reflection densities at 650 nm were measured. As a result, with the element Nos. 12, 16, 17, 18, 19, 20, 21 and 22, no difference was observed between the test results of Lyphocheck Level I and III.

Bilirubin was added to a serum containing 15 μg/ml of theophyllin so as to attain the bilirubin level of 0, 2.5, 5, 10 or 15 μg/ml. On the other hand, for the element Nos. 9, 10, 11, 13, 14 and 15, calibration curves were prepared as in Example 1 using sera with known level of theophyllin. Then each of the sera containing bilirubin, which was prepared as described above was dropped on each of the elements and the theophyllin level was determined by measuring the reflection density at 650 nm and by using the calibration curve prepared as mentioned above. The results are shown in Table 7.

TABLE 7

| Element No. | Bilirubin Level (ug/ml) | | | | |
|---|---|---|---|---|---|
| | 0 | 2.5 | 5 | 10 | 15 |
| 9 | 15 | 14.4 | 13.0 | 11.8 | 11.3 |
| | (100) | (96) | (87) | (79) | (75) |
| 10 | 15 | 14.9 | 14.6 | 14.5 | 14.1 |
| | (100) | (99) | (97) | (97) | (94) |
| 11 | 15 | 14.8 | 14.5 | 14.5 | 14.0 |
| | (100) | (99) | (97) | (97) | (93) |
| 13 | 15 | 14.7 | 14.0 | 13.2 | 11.7 |
| | (100) | (98) | (93) | (88) | (78) |
| 14 | 15 | 14.8 | 14.6 | 14.3 | 14.1 |
| | (100) | (99) | (97) | (95) | (94) |
| 15 | 15 | 14.8 | 14.6 | 14.3 | 14.1 |
| | (100) | (99) | (97) | (95) | (94) |

(The numbers in the parentheses mean the % theophyllin level taking the measured theophyllin level of the sample containing no bilirubin as 100%.)

As is apparent from Table 7, the influence by bilirubin is much smaller in the elements of the present invention (element Nos. 10, 11, 14 and 15) than in the comparative elements (element Nos. 9 and 13).

Although the present invention was described based on the preferred embodiments thereof, it is apparent for those skilled in the art that various modifications can be made without departing from the spirit and scope of the present invention.

We claim:

1. A multilayered assay element comprising:

a support;

a reagent layer formed on the support; and, a spreading layer formed on the reagent layer, said spreading layer having incorporated therein a bilirubin-trapping agent of the formula I

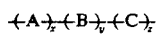    I wherein

A represents a monomer unit represented by one of the formulae II to VII

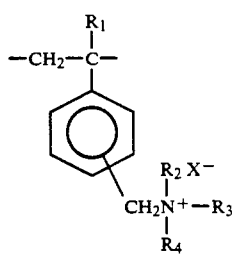    II wherein $R_1$ represents a hydrogen atom or methyl group, $R_2$, $R_3$ and $R_4$, the same or different represent an alkyl, aralkyl, cycloalkyl or cycloaralkyl group, and $X^-$ represents a monovalent anion,

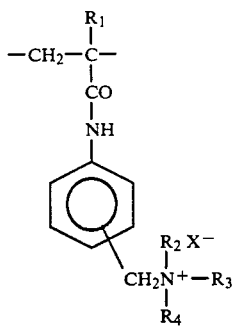    III wherein $R_1$, $R_2$, $R_3$, $R_4$ and $X^-$ have the same meaning as in the formula II,

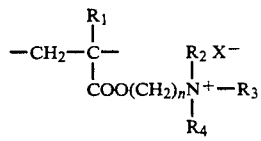    IV wherein $R_1$, $R_2$, $R_3$, $R_4$ and $X^-$ have the same meaning as in the formula II, and n represents an integer of 1 to 4,

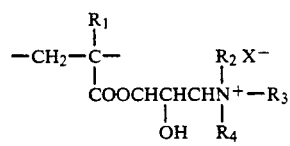    V wherein $R_1$, $R_2$, $R_3$, and $R_4$ and $X^-$ have the same meaning as in the formula II,

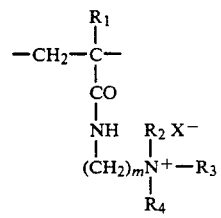    VI wherein $R_1$, $R_2$, $R_3$, $R_4$ and $X^-$ have the same meaning as in the formula II, and m represents an integer of 1 to 4,

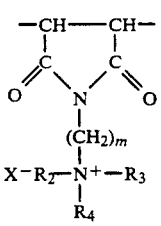    VII wherein $R_1$, $R_2$, $R_3$, $R_4$ and $X^-$ have the same meaning as in the formula II, and m has the same meaning as in the formula VI;

B represents a monomer unit having a copolymerizable unsaturated double bond;

C represents a monomer unit having at least two copolymerizable unsaturated double bonds; and x, y and z represent the number mol% of 100-10, 90-0 and 10-0, respectively.

2. The element of claim 1, wherein the bilirubin-trapping agent is in the form of latex.

3. The element of claim 1, wherein the spreading layer comprises a fibrous material bounded with a binder, and the bilirubin-trapping agent is contained in the spreading layer in the amount of not less than 10% by weight of the binder.

4. The element of claim 3, wherein the ratio of the fibrous material to the binder is 98:2 to 80:20 based on weight.

* * * * *